United States Patent
Brucker et al.

(10) Patent No.: US 6,458,123 B1
(45) Date of Patent: Oct. 1, 2002

(54) ABLATION CATHETER WITH POSITIONAL SENSOR

(75) Inventors: Gregory G. Brucker, Minneapolis; Steven D. Savage, Paynesville, both of MN (US)

(73) Assignee: Biosense Webster, Inc., Miami Lakes, FL (US)

( * ) Notice: Subject to any disclaimer, the term of this patent is extended or adjusted under 35 U.S.C. 154(b) by 0 days.

(21) Appl. No.: 09/561,247

(22) Filed: Apr. 27, 2000

(51) Int. Cl.[7] .............................................. A61B 18/18
(52) U.S. Cl. ........................ 606/41; 607/96; 607/104; 607/105
(58) Field of Search ...................... 606/32–50; 607/96, 607/98, 99–106, 113

(56) References Cited

U.S. PATENT DOCUMENTS

| | | |
|---|---|---|
| 5,334,193 A | 8/1994 | Nardella |
| 5,391,199 A | 2/1995 | Ben-Haim |
| 5,431,649 A | 7/1995 | Mulier et al. |
| 5,443,489 A | 8/1995 | Ben-Haim |
| 5,462,521 A | 10/1995 | Brucker et al. |
| 5,480,422 A | 1/1996 | Ben-Haim |
| 5,546,951 A | 8/1996 | Ben-Haim |
| 5,558,091 A | 9/1996 | Acker et al. |
| 5,568,809 A | 10/1996 | Ben-Haim |
| 5,643,197 A | 7/1997 | Brucker et al. |
| 5,697,927 A | 12/1997 | Imran et al. |
| 5,735,847 A | 4/1998 | Gough et al. |
| 5,741,249 A | * 4/1998 | Moss et al. ................... 606/33 |
| 5,776,176 A | * 7/1998 | Rudie ........................ 607/101 |
| 5,792,140 A | 8/1998 | Tu et al. |
| 5,800,428 A | 9/1998 | Nelson et al. |
| 5,913,856 A | 6/1999 | Chia et al. |
| 5,919,188 A | 7/1999 | Shearon et al. |
| 5,938,659 A | 8/1999 | Tu et al. |

FOREIGN PATENT DOCUMENTS

| | | |
|---|---|---|
| EP | 0928601 | 7/1999 |
| WO | WO 96/34570 | 11/1996 |

* cited by examiner

Primary Examiner—Rosiland S. Kearney
(74) Attorney, Agent, or Firm—George H. Gerstman; Seyfarth Shaw

(57) ABSTRACT

An ablation catheter is provided which comprises a steerable catheter including a distal portion and a proximal portion. An ablation electrode is carried by the distal portion, with the ablation electrode having structure defining an interior space and having at least one aperture. A positional sensor is located in the interior space, wherein the proximal portion is connected to a source of cooling liquid which flows out of the aperture. The ablation catheter provides a suitable flow of fluid through the aperture while providing a space or volume sufficiently large for placement of a positional sensor.

23 Claims, 2 Drawing Sheets

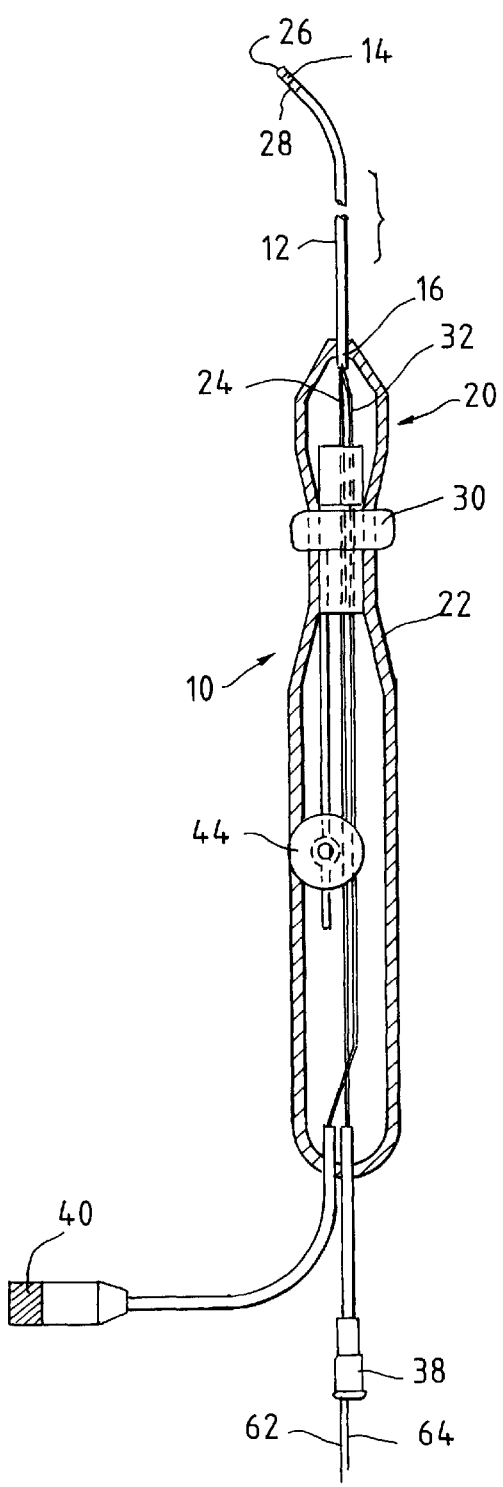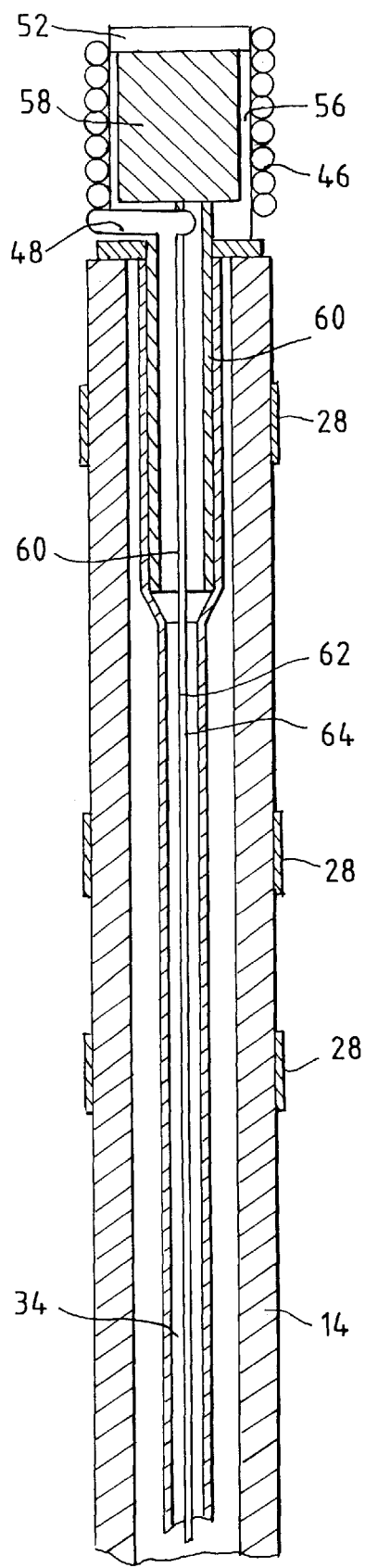

ABLATION CATHETER WITH POSITIONAL SENSOR

FIELD OF THE INVENTION

The present invention concerns a novel ablation catheter and, more particularly, a steerable catheter carrying a positional sensor for mapping.

BACKGROUND OF THE INVENTION

Catheter ablation has become a well-known technique for treating various a flexible tubular electrode that is selectively extendable from a distal end of a catheter body, have been used in treating cardiac arrhythmias. An example of an ablation catheter system utilizing an extendable electrode is disclosed in Nelson et al. U.S. Pat. No. 5,800,428.

In treating tachyarrhythmias using cardiac ablation techniques, discrete, 4 or 8 mm electrodes are placed in the heart under fluoroscopic and electrophysiological guidance. By nature, these are not very precise location tools. Often, during these procedures, it is highly desirable to return to the location of a previous ablation and determine the effectiveness or completeness of a lesion. Because the area has been electrically damaged, EP signals are either non-existent or their amplitude has been reduced significantly to the point of being unusable. In addition, because fluoroscopy provides only a two dimensional view of a three dimensional space, returning within several millimeters to a previous location is not possible. Thus, it would be helpful to have a different means to establish the location of a catheter tip within a cardiac chamber. At least one technology exists in which a sensor is placed within the catheter structure and this sensor interacts with external devices to spherically triangulate and determine the position of the sensor. The accuracy of such methods in part depends on the proximity of the sensor to the tip.

One difficulty in attaching a sensor to current catheter designs is finding adequate space near the tip to place the sensor which in some case can be half the volume of the tip. In solid tip electrode designs, a mass of metal is needed to provide passive cooling during ablation. In cooled tip electrode designs, flow passages are needed to transport fluid to the distal regions of the tip. Because of inefficient cooling and resultant high flow rates, these passages consume most of the available space in both the tip electrode and shaft.

In Brucker et al. U.S. Pat. No. 5,643,197, a porous metal structure was designed to reduce the coolant flow to a fraction of the requirement for other tips. However, the mechanical integrity of the porous tip is predicated on having a thicker cross sectional area which precludes the placement of a sensor near the tip.

It is an object of the present invention to provide an ablation catheter in which a positioning sensor is efficiently located within the tip to provide information on the location of the catheter tip in the heart.

Another object of the present invention is to provide an ablation catheter in which there is an efficient flow of cooling fluid through the electrode tip while still providing an efficient location for the positioning sensor carried by the electrode.

A still further object of the invention is to provide an ablation catheter using an electrode which perfuses fluid to cool the tip and to form a protective layer which minimizes or eliminates contact with blood.

Another object of the present invention is to provide an ablation catheter in which there is an effective means to establish the location of the electrode tip within a cardiac chamber.

A further object of the present invention is to provide a catheter for creating a focal lesion using RF energy which utilizes an ablation electrode that provides efficient fluid disbursement and also efficient cooling of the electrode tip.

Other objects and advantages of the invention will become apparent as the description proceeds.

SUMMARY OF THE INVENTION

In accordance with the present invention, an ablation catheter is provided which comprises a steerable catheter including a distal portion and an ablation electrode carried by the distal portion. In one embodiment, the ablation electrode comprises a helically shaped tube and a positional sensor is located in the space defined by the helically shaped tube.

In one embodiment, the helically shaped tube has a proximal end and distal end, with the proximal end being coupled to a source of cooling fluid. The distal end is adapted to enable cooling fluid to flow between windings of the helically shaped tube, to form an insulating layer around the distal end to reduce impedance rises caused by blood coagulation.

In another embodiment, the helically shaped tube defines openings for exit of the cooling fluid as it passes through the tube. In that embodiment, the helically shaped tube may be wound so that each turn of the tube touches neighboring turns.

In the illustrative embodiments, the ablation catheter includes a proximal portion comprising a handle and a sliding mechanism for extending the distal portion.

In another embodiment, an ablation catheter is provided which comprises a steerable catheter including a distal portion with an ablation electrode carried by the distal portion. In this embodiment, the ablation electrode comprises a hollow electrode formed of a metal sheet defining a plurality of holes. A positional sensor is located in the spaced defined by the hollow electrode. A support flange couples the hollow electrode to a cooling tube with the support flange defining an opening for enabling fluid flow through the opening, then along the positional sensor before exiting the hollow electrode via the defined holes.

A more detailed explanation of the invention is provided in the following description and claims, and is illustrated in the accompanying drawings.

DESCRIPTION OF THE DRAWINGS

FIG. 1 is a schematic representation of an RF ablation catheter system in accordance with the principles of the present invention.

FIG. 2 is a cross-sectional view of the distal end of the catheter of FIG. 1.

DETAILED DESCRIPTION OF ILLUSTRATIVE EMBODIMENTS

Figure 3:
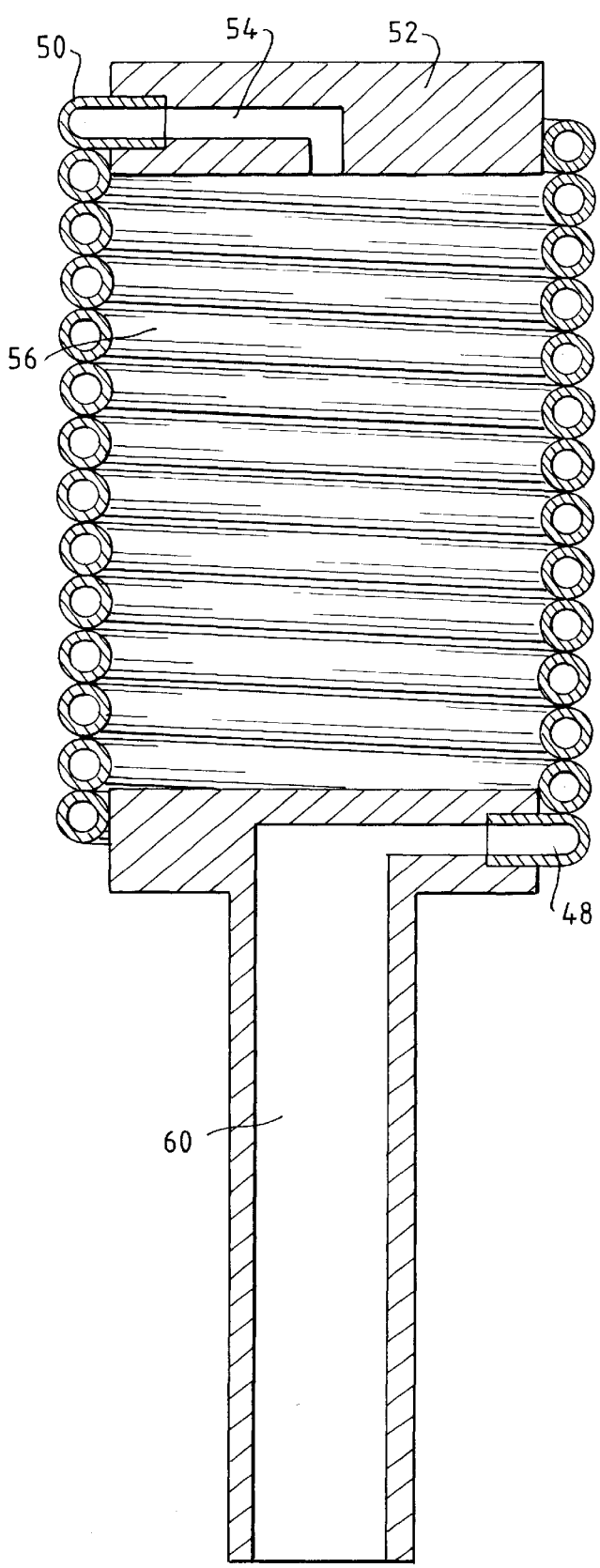
FIG. 3 is an enlarged cross sectional view of the electrode of the catheter of FIGS. 1 and 2.
Figure 4:
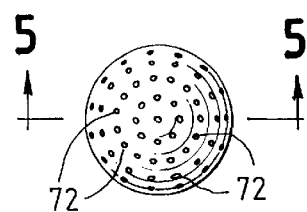
FIG. 4 is an end view of an RF ablation catheter in accordance with another embodiment of the present invention.

Referring to the drawings, FIG. 1 illustrates an RF catheter ablation system 10 including a flexible, elongated catheter body 12 having a distal end 14 and a proximal end 16, and mechanism 20 for operating the catheter system. The system includes a handle 22 for manipulating and also preferably extending catheter body 12 and structure 24 for providing a cooling fluid, preferably saline, which passes through catheter 12 to electrode 26 at the distal end 14.

Catheter 12 is a steerable catheter containing distal section 14 which articulates and to which are attached ring electrodes 28, a braided shaft section (not shown) and handle 22 with a sliding mechanism 30 for articulating the distal portion 14 of catheter 12. It should be understood that various techniques known in the catheter art for manipulating or steering a distal tip section of a catheter may be employed with the present invention.

Electrical line 32 provides the RF energy. The cooling fluid structure 24 and the RF energy delivery line 32 are disposed within lumen 34 of catheter body 12. Fluid is introduced through fluid interface port 38 and an RF energy source is coupled to an electrical interface port 40. A tension adjustment mechanism 44 is used to adjust sliding mechanism 30 and thereby control the feel of the catheter system.

The ablation electrode 26 is made from a helically shaped hypodermic tube 46. In one embodiment, coil 46 is wound so that each turn of the tubing touches neighboring turns. The proximal end of the tubing connects to a fluid tube 48 and the distal end of the tubing 50 is capped with a circular cap 52 that defines a passageway 54 extending from the distal end of the tubing into a space 56 in which positional sensor 58 is located.

The coiled tip electrode is attached to the distal end of catheter 14 by a support flange 60 which is coaxial with cooling tube 34. In the embodiment illustrated in FIG. 3, in which each turn of the tubing touches neighboring turns, holes are drilled in the hypodermic tubing so that the cooling fluid will flow through the hypodermic tubing with some of the fluid exiting the hypodermic tubing via the drilled holes while the remaining fluid exits the tip after it passes through the tubing. The exiting action forms an insulating layer around the tip to reduce impedance rises caused by blood coagulation.

In another embodiment, the coil is wound so that each turn of the tubing is spaced slightly from neighboring turns. In this embodiment, water flows through the hypodermic tubing, cooling the tubing and then flows around the positional sensor that is positioned within the spaced defined by the tubing and then exits the catheter by flowing between the windings of the tubing. Like the previous embodiment, the exiting action forms an insulating layer around the tip to reduce impedance rises caused by blood coagulation.

Wires 62 and 64 from the positional sensor extend through the support flange 60 and the cooling tube 34. Although not illustrated, these wires will be connected to an external device to determine the position of the catheter tip.

Figure 5:
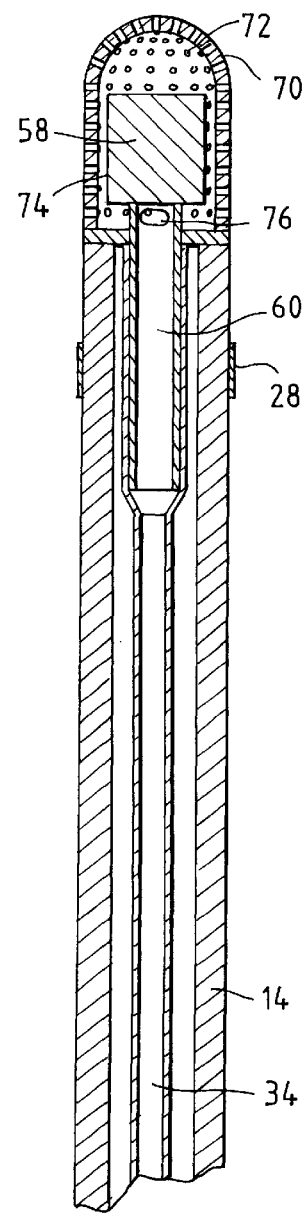
FIG. 5 is a cross-sectional view of the distal end of an RF ablation catheter, taken along the plane of the line 5—5 of FIG. 4.

In the FIG. 5 embodiment, a hollow cup-shaped electrode is provided comprising a deep drawn metal sheet 70 in which holes 72 are punched. Hollow electrode 70 is attached to the distal end of the catheter 14 via a support flange 60. The annular space formed by the cup-shaped electrode 70 and flange 60 are suitable for the location of a positional sensor 58 therein, with wires (not shown) running through cooling lumen 34. Sufficient space 74 is provided around positional sensor 58 to permit flow of fluid to protect the sensor from heat and to cool the tip electrode. Fluid flows into the annular space 74 from the cooling lumen 34, through an opening 76 in the support flange 60, and then along the sensor 58 before exiting the tip via holes 72. The flow exiting the tip forms an insulating layer around the tip to reduce the incidence of coagulum formation. Although various fluids could be used in accordance with the invention, it is preferred that saline be used to cool the tip and to form a protective layer which minimizes or eliminates contact with blood.

It can be seen that a novel RF ablation catheter has been provided which allows the placement of a positioning sensor in an effective location for providing information concerning the location of the catheter tip in the heart. Although illustrative embodiments of the invention have been shown and described, it is to be understood that various modifications and substitutions may be made by those skilled in the art without departing from the novel spirit and scope of the present invention.

What is claimed:

1. An ablation catheter which comprises:
   a steerable catheter including a distal portion;
   an ablation electrode carried by said distal portion, said ablation electrode comprising a helically shaped tube; and
   a positional sensor located in a space defined by said helically shaped tube.

2. An ablation catheter as defined in claim 1, in which said helically shaped tube has a proximal end and a distal end, said proximal end being coupled to a source of cooling fluid.

3. An ablation catheter as defined in claim 2, said distal end including structure to enable cooling fluid to flow between windings of said helically shaped tube, to form an insulating layer around said distal end to reduce impedance rises caused by blood coagulation.

4. An ablation catheter as defined in claim 2, said helically shaped tube defining openings for exit of said cooling fluid as it passes through said tube.

5. An ablation catheter as defined in claim 2, in which said cooling fluid flows through said helically shaped tube, cooling the tubing and then flows around the positional sensor and exits the catheter by flowing between windings of said helically shaped tube.

6. An ablation catheter as defined in claim 1, said helically shaped tube being wound so that each turn of the tube touches neighboring turns.

7. An ablation catheter as defined in claim 1, in which said steerable catheter includes a proximal portion comprising a handle; and a sliding mechanism for extending said distal portion.

8. An ablation catheter as defined in claim 1, in which said distal portion is extendable.

9. An ablation catheter which comprises:
   a steerable catheter including a distal portion which is extendable;
   an ablation electrode carried by said distal portion, said ablation electrode comprising a helically shaped tube, said helically shaped tube having a proximal end and a distal end;
   a positional sensor located in a space defined by said helically shaped tube; and
   said proximal end being coupled to a source of cooling fluid whereby the cooling fluid flows through said helically shaped tube, cooling the tubing and then flows around the positional sensor and exits the catheter by flowing between windings of said helically shaped tube.

10. An ablation catheter as defined in claim 9, in which said steerable catheter includes a proximal portion comprising a handle; and a sliding mechanism for extending said distal portion.

11. An ablation catheter as defined in claim 9, said helically shaped tube defining openings for exit of said cooling fluid as it passes through said tube.

12. An ablation catheter as defined in claim 9, said helically shaped tube being wound so that each turn of the tube touches neighboring turns.

13. An ablation catheter which comprises:

a steerable catheter including a distal portion which is extendable;

an ablation electrode carried by said distal portion, said ablation electrode comprising a helically shaped tube, said helically shaped tube being wound so that each turn of the tube touches neighboring turns and having a proximal end and a distal end;

said helically shaped tube defining openings for exit of said cooling fluid as it passes through said tube;

a positional sensor located in a space defined by said helically shaped tube;

said proximal end being coupled to a source of cooling fluid whereby said cooling fluid flows in said helically shaped tube and exits from said defined openings.

14. An ablation catheter which comprises:

a steerable catheter including a proximal portion comprising a handle, a distal portion, and a sliding mechanism for extending said distal portion;

an ablation electrode carried by said distal portion, said ablation electrode comprising a helically shaped tube;

said helically shaped tube having a proximal end and a distal end;

said proximal end being coupled to a source of cooling fluid;

said helically shaped tube defining openings for exit of said cooling fluid as it passes through said tube; and said helically shaped tube being wound so that each turn of the tube touches neighboring turns.

15. An ablation catheter which comprises:

a steerable catheter including a distal portion;

an ablation electrode carried by said distal portion, said ablation electrode comprising a hollow electrode formed of a metal sheet defining a plurality of holes; and a positional sensor located in a space defined by said hollow electrode.

16. An ablation catheter as defined in claim 15, including a support flange coupling said hollow electrode to a cooling tube.

17. An ablation catheter as defined in claim 16, in which said support flange defines an opening for enabling fluid flow through said opening, then along said positional sensor before exiting said hollow electrode via said defined holes.

18. An ablation catheter as defined in claim 15, in which sufficient space is defined between said positional sensor and said hollow electrode to permit flow of fluid to protect the sensor from heat and to cool said hollow electrode.

19. An ablation catheter comprising:

a steerable catheter including a distal portion and a proximal portion;

an ablation electrode carried by said distal portion, said ablation electrode having structure defining an interior space and having at least one aperture; and a positional sensor located in the interior space;

whereby said proximal portion is connected to a source of cooling fluid which flows out of said at least one aperture.

20. The ablation catheter of claim 19 wherein said ablation electrode comprises a helically shaped tube.

21. The ablation catheter of claim 20 wherein the at least one aperture is oriented to allow flow of said cooling fluid transversely to a longitudinal axis of said steerable catheter.

22. The ablation catheter of claim 19 wherein said ablation electrode comprises a hollow electrode formed of a metal sheet defining a plurality of apertures.

23. The ablation catheter of claim 19 wherein the at least one aperture is oriented to allow flow of said cooling fluid transversely to a longitudinal axis of said steerable catheter.

* * * * *